(12) United States Patent
Seidling et al.

(10) Patent No.: US 11,655,994 B2
(45) Date of Patent: May 23, 2023

(54) ANTIMICROBIAL COMPOSITION INCLUDING AN ACYL LACTYLATE AND A GLYCOL AND METHODS OF INHIBITING MICROBIAL GROWTH UTILIZING THE SAME

(71) Applicant: Kimberly-Clark Worldwide, Inc., Neenah, WI (US)

(72) Inventors: Jeffery R. Seidling, Neenah, WI (US); Paige N. Anunson, Neenah, WI (US); Corey T. Cunningham, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 68 days.

(21) Appl. No.: 16/615,887

(22) PCT Filed: May 31, 2017

(86) PCT No.: PCT/US2017/035173
§ 371 (c)(1),
(2) Date: Nov. 22, 2019

(87) PCT Pub. No.: WO2018/222184
PCT Pub. Date: Dec. 6, 2018

(65) Prior Publication Data
US 2021/0071895 A1 Mar. 11, 2021

(51) Int. Cl.
| | | |
|---|---|---|
| *A61K 8/37* | (2006.01) | |
| *A61K 8/34* | (2006.01) | |
| *A61K 8/02* | (2006.01) | |
| *A61Q 17/00* | (2006.01) | |
| *F24F 11/56* | (2018.01) | |
| *F24F 11/72* | (2018.01) | |
| *F24F 11/30* | (2018.01) | |
| *F24F 110/50* | (2018.01) | |
| *F24F 110/12* | (2018.01) | |

(52) U.S. Cl.
CPC .............. *F24F 11/56* (2018.01); *F24F 11/30* (2018.01); *F24F 11/72* (2018.01); *F24F 2110/12* (2018.01); *F24F 2110/50* (2018.01)

(58) Field of Classification Search
None
See application file for complete search history.

(56) References Cited

U.S. PATENT DOCUMENTS

| | | |
|---|---|---|
| 4,822,601 A | 4/1989 | Goode et al. |
| 5,951,991 A | 9/1999 | Wagner et al. |
| 6,258,368 B1 | 7/2001 | Beerse et al. |
| 6,284,259 B1 | 9/2001 | Beerse et al. |
| 6,730,621 B2 | 5/2004 | Gott et al. |
| 6,797,399 B2 | 9/2004 | Weuthen et al. |
| 6,797,400 B2 | 9/2004 | Weuthen et al. |
| 6,992,054 B2 | 1/2006 | Lee et al. |
| 7,195,771 B1 | 3/2007 | Hsu et al. |
| 7,592,019 B2 | 9/2009 | Drucks et al. |
| 7,608,573 B1 | 10/2009 | Scheuing et al. |
| 7,811,596 B2 | 10/2010 | Weuthen et al. |
| 8,940,675 B2 | 1/2015 | Marsh et al. |
| 2002/0155281 A1* | 10/2002 | Lang .................. C11D 3/3738 442/415 |
| 2003/0022572 A1 | 1/2003 | Gott et al. |
| 2006/0039956 A1 | 2/2006 | Hensen et al. |
| 2006/0105937 A1 | 5/2006 | Duran et al. |
| 2006/0122082 A1 | 6/2006 | Paul |
| 2006/0276541 A1 | 12/2006 | Tautvydas et al. |
| 2007/0110791 A1 | 5/2007 | Myhra |
| 2007/0155645 A1 | 7/2007 | Eisfeld et al. |
| 2007/0160651 A1 | 7/2007 | Mueller et al. |
| 2007/0212401 A1 | 9/2007 | Masse |
| 2008/0241204 A1* | 10/2008 | Leikauf .................. A61Q 19/10 510/159 |
| 2010/0239624 A1* | 9/2010 | Myhra ................. A61K 8/0208 424/401 |
| 2010/0239634 A1* | 9/2010 | Shimp ..................... A61P 19/08 424/423 |
| 2012/0128614 A1 | 5/2012 | Rieth et al. |
| 2014/0171351 A1* | 6/2014 | Wenzel .................. A61Q 19/10 510/157 |
| 2015/0017218 A1 | 1/2015 | Pettigrew et al. |
| 2015/0086659 A1 | 3/2015 | Klofta et al. |
| 2017/0348203 A1* | 12/2017 | Schelges ................. C07C 31/18 |

FOREIGN PATENT DOCUMENTS

| | | | |
|---|---|---|---|
| CN | 105411870 A | | 3/2016 |
| KR | 20140092635 A | * | 7/2014 |
| KR | 1020140092635 A | | 7/2014 |
| RU | 2537235 C2 | | 12/2014 |
| WO | 9966793 A1 | | 12/1999 |

* cited by examiner

*Primary Examiner* — Danah Al-Awadi
(74) *Attorney, Agent, or Firm* — Kimberly-Clark Worldwide, Inc.

(57) ABSTRACT

Antimicrobial compositions and methods for inhibiting microbial growth are disclosed. The antimicrobial compositions can include an acyl lactylate, a glycol, and a carrier. The carrier can include water. Water can form at least about 90% by weight of the composition.

2 Claims, No Drawings

ANTIMICROBIAL COMPOSITION INCLUDING AN ACYL LACTYLATE AND A GLYCOL AND METHODS OF INHIBITING MICROBIAL GROWTH UTILIZING THE SAME

TECHNICAL FIELD

Disclosed are antimicrobial compositions and methods of inhibiting microbial growth. More specifically, disclosed is an antimicrobial composition that includes an acyl lactylate and a glycol and methods of utilizing the same to inhibit microbial growth. The antimicrobial composition may be applied to or incorporated into articles such as wipes, or into ointments, lotions, creams, salves, aerosols, gels, suspensions, sprays, foams, washes, or the like.

BACKGROUND OF THE DISCLOSURE

Preservatives are an often utilized component in cosmetic, pharmaceutical, and personal care products to ensure that a product stays fresh on the shelf, doesn't experience spoilage, and remains free from microbial growth. In particular, because personal care products may be used to directly contact skin or mucosa such as around body orifices where the potential for transfer of materials from the product to the consumer may be a concern, it is generally good practice to reduce contamination of the product in every possible way. The need to control microbiological growth in personal care products is particularly acute in water based products such as non-ionic oil-in-water emulsions and in pre-impregnated wipes such as wet wipes.

Multiple options for preservatives that prevent microbial growth, such as formaldehyde donors or parabens, have existed throughout history and these preservatives were highly efficacious and allowed for relatively easy preservation of personal care products. Recently, traditional preservatives have been less desirable components in personal care products in view of new regulations and consumer perceptions, thus limiting the options for preserving and preventing microbial growth in certain products. Additionally, reducing the number of ingredients for preserving and preventing microbial growth in products provides increased consumer understanding and can provide additional confidence in purchasing decisions. Furthermore, reducing the number of ingredients in a composition can reduce complexity in manufacturing of the composition.

While alternative preservatives have been explored, each carry limitations. For example, some organic acids and their derivatives have been used for their preservative effect, however, organic acids tend to have an inherent odor, thus limiting the concentration that can be used without negatively affecting the overall olfactory perception of the product. Additionally, organic acids often are only efficacious in acid form, thus limiting their use to compositions having a narrow and low pH range, and also have limited water solubility.

Thus, there remains a need for antimicrobial compositions that include alternative preservatives that can be used in a composition to inhibit microbial growth in a product.

SUMMARY OF THE DISCLOSURE

In one aspect of the disclosure, a composition is provided. The composition can include an acyl lactylate, a glycol, and a carrier. The carrier can comprise water. Water can comprise at least about 90% by weight of the composition.

In another aspect of the disclosure, a composition can consist of an acyl lactylate, a glycol, and a carrier. The carrier can include water. Water can form between about 90% and about 99.8% by weight of the composition. The composition can optionally include one or more ingredients selected from the group consisting of a pH adjusting ingredient and a fragrance.

In yet another aspect of the disclosure, a wipe is provided. The wipe can include a substrate. The wipe can also include a composition applied to the substrate. The composition can include an acyl lactylate, a glycol, and a carrier. The carrier can include water. Water can include at least about 50% by weight of the composition.

In still another aspect of the disclosure, a method of inhibiting microbial growth in a product is provided. The method can include providing a composition. The composition can include an acyl lactylate, a glycol, and a carrier. The method can include providing a product. The method can also include applying the composition to the product to inhibit microbial growth in the product.

DETAILED DESCRIPTION OF THE DISCLOSURE

The present disclosure is directed to antimicrobial compositions and methods of inhibiting microbial growth in which the antimicrobial compositions include an acyl lactylate and a glycol. The antimicrobial compositions could be utilized in a variety of cosmetic, pharmaceutical, and other personal care products. Suitable products could include, but are not limited to: shampoo, conditioner, soaps, moisturizers, skin protective, skin restorative and skin strengthening products, hand sanitizers, skin and body cleansers, deodorants, sunscreens, lip balms, lip sticks and the like. These products could take a variety of forms including but not limited to water-thin liquids, aqueous solutions, gels, balms, lotions, ointments, suspensions, creams, milks, salves, ointments, pastes, powders, aerosols, sprays, mists, mousses, emulsions, oils, foams, washes, solid sticks, aerosols, water, oil or silicone solutions or emulsions, including water in oil, oil in water, silicone in water, water in silicone and the like. Additionally, as will be described in further detail below, the forms of these products may be used in conjunction with a substrate, such that the solution may be added to the substrate for delivery. Suitable substrate based products include, but are not limited to: wipes, facial tissue, bath tissue, paper towels, napkins, diapers, diaper pants, feminine hygiene products (tampons, pads), gloves, socks, masks or combinations thereof.

Within each of the above envisioned products, the antimicrobial compositions including an acyl lactylate and a glycol could be combined with a variety of other ingredients utilized in cosmetic, pharmaceutical and other personal care products. Suitable ingredients, some of which will be described in further detail herein, can come from a broad category range including, but not limited to aqueous solvents, non-aqueous solvents, humectants, emollients, surfactants, emulsifiers, sequestrants, chelators, preservatives, pH modifiers (or pH adjusting ingredient), combinatorial preservatives/antimicrobial agents, disinfectants, colorants, rheology modifiers, antioxidants, anti-parasitic agents, anti-pruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, deodorants, antiperspirants, fragrance, and various other optional ingredients as are known by one skilled in the art.

Acyl Lactylates & Glycols

The antimicrobial compositions of this disclosure include an acyl lactylate and a glycol that are utilized to provide antimicrobial activity. Table 1 below shows a variety of acyl lactylates and glycols that were explored for their antimicrobial activity.

TABLE 1

| Listing of acyl lactylates and glycols selected for testing | | | | |
|---|---|---|---|---|
| Category | INCI Name | Trade Name | Vendor | Form |
| Acyl Lactylate | Sodium Lauroyl Lactylate | Dermosoft ® SLL | Dr. Streatmans | Thick gel |
| Acyl Lactylate | Sodium Caproyl/Lauroyl Lactylate | Decalact | Dr. Streatmans | Thick gel |
| Acyl Lactylate | Sodium Isostearoyl Lactylate | Pationic ISL | Rita | Thick gel |
| Acyl Lactylate | Sodium Stearoyl Lactylate | Pationic ISL | Rita | Solid |
| Acyl Lactylate | Sodium Behenoyl Lactylate | Pationic ISL | Rita | Solid |
| Glycol | Methylpropanediol | DUB DIOL | Stearinerie Dubois | Liquid |
| Glycol | 1,2-Hexanediol | Lexgard ® H | Inolex | Liquid |
| Glycol | Isopentyldiol | Isoprene Glycol | Barnet | Liquid |
| Glycol | 1,2-Propanediol | Zemea ® | Dupont Tate and Lyle | Liquid |
| Glycol | Propylene Glycol | Propylene Glycol USP | Lonza | Liquid |

In an initial experiment, a representative acyl lactylate (Sodium Lauroyl Lactylate) was combined with a representative glycol in a concentration experiment to determine synergistic effects and dose response. Sodium Lauroyl Lactylate was added at a decreasing gradient beginning at 1% in sample 1 (S1) and decreasing to 0% in sample 11 (S11), as shown in Table 2. Methylpropanediol was combined with the Sodium Lauroyl Lactylate at an increasing gradient accordingly from 0% to 1% such that the sum of Sodium Lauroyl Lactylate and Methylpropanediol always equals 1% in each formulation. The remaining 99% of each formulation is made up of a carrier (i.e., water) and pH adjusted with a pH adjusting ingredient (i.e., citric acid) to the values recorded in Table 2. Antimicrobial activity reported in Table 2 was determined by an initial antimicrobial screening protocol, a modified AlamarBlue™ outgrowth assay, and values reported are average $LOG_{10}$ CFU/well reductions of inoculums of *Burkholderia cepacia* for values recorded over 72 hours.

TABLE 2

| Performance of various samples including sodium lauroyl lactylate and methylpropanediol | | | | | | | | | | | | | | |
|---|---|---|---|---|---|---|---|---|---|---|---|---|---|---|
| Component | (+) C | (−) C | S1 | S2 | S3 | S4 | S5 | S6 | S7 | S8 | S9 | S10 | S11 | S12 |
| Sodium Lauroyl Lactylate (% wt/wt) | | | 0.00 | 0.05 | 0.15 | 0.25 | 0.35 | 0.50 | 0.65 | 0.75 | 0.85 | 0.95 | 1.00 | 0.50 |
| Methylpropanediol (% wt/wt) | | | 1.00 | 0.95 | 0.85 | 0.75 | 0.65 | 0.50 | 0.35 | 0.25 | 0.15 | 0.05 | 0.00 | 0.50 |
| Water (% wt/wt) | | | 99.00 | 99.00 | 99.00 | 99.00 | 99.00 | 99.00 | 99.00 | 99.00 | 99.00 | 99.00 | 99.00 | 99.00 |
| pH | | | 4.46 | 4.55 | 4.45 | 4.58 | 4.55 | 4.54 | 4.49 | 4.53 | 4.50 | 4.54 | 4.49 | 5.43 |
| Average $Log_{10}$ CFU/well reduction | 4.96 | 1.91 | 0.84 | 0.97 | 1.44 | 1.69 | 2.97 | 3.90 | 4.92 | 4.89 | 4.91 | 4.91 | 4.91 | 1.29 |

As evidenced by samples 1-12 (S1-S12) in Table 2, the efficacy against *B. cepacia* displays values above the negative control ("(−) C") beginning at concentrations of 0.35% Sodium Lauroyl Lactylate and 0.65% Methylpropanediol and at a pH of approximately 4.50, the antimicrobial effectiveness increasing as the concentration of Sodium Lauroyl Lactylate increased to 1.00%. When the pH is adjusted to 5.43 as in Sample 12 (S12), the antimicrobial effectiveness is depressed significantly in comparison to Sample 6, with identical composition, but a pH of 4.54. Accordingly, the pH of the composition also can provide benefits for increasing the antimicrobial effectiveness of the composition.

The formulation of sample 6 (S6) in Table 2, a 1:1 ratio of acyl lactylate to glycol, was chosen for further experimentation as it provides more antimicrobial effectiveness than did the negative control, but not complete reduction of the bacteria. This performance criteria was noted to be helpful for further screening to differentiate between good and excellent performing compositions.

An advantage of compositions including an acyl lactylate and a glycol is the reduction of viscosity that is present in acyl lactylates, which is rather high and increases difficulty in processing. Table 3 shows the reduction in viscosity of several acyl lactylates when in a 1:1 mixture with various glycols. Of course, it is expected that a lowering of viscosity of the acyl lactylates would be realized in ratios of acyl lactylates:glycols other than 1:1 as well.

TABLE 3

| Viscosity of select acyl lactylates alone and in combination with various glycols | | | |
|---|---|---|---|
| Sample Name | Ratio | Parameters | Viscosity (cP) |
| Sodium Caproyl/Lauroyl Lactylate | N/A | Brookfield 95, 5 RPM, 25° C. | 1,192,000 |
| Sodium Lauroyl Lactylate | N/A | Brookfield 95, 5 RPM, 25° C. | 1,520,000 |
| Sodium Isostearoyl Lactylate | N/A | Brookfield 95, 5 RPM, 25° C. | 1,080,000 |
| Sodium Caproyl/Lauroyl Lactylate + Methylpropanediol | 1:1 | Brookfield 93, 35 RPM, 25° C. | 914.3 |
| Sodium Caproyl/Lauroyl Lactylate + 1,2-Hexanediol | 1:1 | Brookfield 93, 35 RPM, 25° C. | 685.7 |

TABLE 3-continued

Viscosity of select acyl lactylates alone and in combination with various glycols

| Sample Name | Ratio | Parameters | Viscosity (cP) |
|---|---|---|---|
| Sodium Caproyl/Lauroyl Lactylate + Propylene Glycol | 1:1 | Brookfield 93, 35 RPM, 25° C. | 457.1 |
| Sodium Lauroyl Lactylate + Methylpropanediol | 1:1 | Brookfield 93, 35 RPM, 25° C. | 914.3 |
| Sodium Lauroyl Lactylate + Propylene Glycol | 1:1 | Brookfield 93, 35 RPM, 25° C. | 457.1 |
| Sodium Isostearoyl Lactylate + 1,2-Hexanediol | 1:1 | Brookfield 93, 35 RPM, 25° C. | 685.7 |
| Sodium Isostearoyl Lactylate + Propylene Glycol | 1:1 | Brookfield 93, 35 RPM, 25° C. | 457.1 |

Preservative Efficacy Testing, as described in detail in the Test Methods section herein, was undertaken to look at the antimicrobial effectiveness of various combinations of acyl lactylates and glycols in a carrier solution of water. The samples as shown in Table 4 were each prepared such that the acyl lactylate had a concentration of 0.5% by weight of the composition, the glycol had a concentration of 0.5% by weight of the composition, and 99% by weight of the composition was water. The compositions were then all pH adjusted to a pH of 4.5 with citric acid (qs). The samples were then coated on coform wipes at an add-on of 330%. Sodium Caproyl/Lauroyl Lactylate was tested in a sample alone (i.e., without being in combination with a glycol) for Preservative Efficacy Testing due to its strong inherent odor.

TABLE 4

Sample code list for Preservative Efficacy Testing

| Sample | Components | Concentration (%) | Add-on (%) |
|---|---|---|---|
| A | Sodium Isostearoyl Lactylate | 0.5 | 330 |
|   | Propylene Glycol | 0.5 | 330 |
| B | Sodium Isostearoyl Lactylate | 0.5 | 330 |
|   | 1,2-Hexanediol | 0.5 | 330 |
| C | Sodium Caproyl/Lauroyl Lactylate | 0.5 | 330 |
|   | Methylpropanediol | 0.5 | 330 |
| D | Sodium Caproyl/Lauroyl Lactylate | 0.5 | 330 |
|   | Isopentyldiol | 0.5 | 330 |
| E | Sodium Caproyl/Lauroyl Lactylate | 0.5 | 330 |
|   | Propylene Glycol | 0.5 | 330 |
| F | Sodium Caproyl/Lauroyl Lactylate | 0.5 | 330 |
|   | 1,2-Hexanediol | 0.5 | 330 |
| G | Sodium Lauroyl Lactylate | 0.5 | 330 |
|   | Propylene Glycol | 0.5 | 330 |
| H | Sodium Lauroyl Lactylate | 0.5 | 330 |
|   | 1,2-Hexanediol | 0.5 | 330 |
| I | Sodium Lauroyl Lactylate | 0.5 | 330 |
| J | Sodium Isostearoyl Lactylate | 0.5 | 330 |
| K | 1,2-Hexanediol | 0.5 | 330 |
| L | Methylpropanediol | 0.5 | 330 |
| M | Propylene Glycol | 0.5 | 330 |
| N | Isopentyldiol | 0.5 | 330 |

Table 5 lists the results of the Preservative Efficacy Testing against various fungi and bacteria for the Samples A-N listed in Table 4 and described above. In Table 5, 'O' indicates a passing result, 'X' indicates a failure, and X*' indicates a failure and that Day 28 testing was not completed due to failures detected at Day 14.

TABLE 5

Results of Preservative Efficacy Testing on Samples A-N on coform wipes

| | Organism | | | | | | | | | | | |
|---|---|---|---|---|---|---|---|---|---|---|---|---|
| | S. aureus | | E. coli | | P. aeruginosa | | C. albicans | | A. brasiliensis | | B. cepacia | |
| Sample | Day 14 | Day 28 | Day 14 | Day 28 | Day 14 | Day 28 | Day 14 | Day 28 | Day 14 | Day 28 | Day 14 | Day 28 |
| A | Failure - mold growth prior to starting Preservative Efficacy Testing | | | | | | | | | | | |
| B | O | O | O | O | X | O | O | O | O | O | X | O |
| C | O | O | O | O | O | X | O | X | O | X | O | O |
| D | O | X | O | X* | X | X* | O | X* | O | X* | O | X* |
| E | O | X* | O | X* | X | X* | O | X* | O | X* | X | X* |
| F | O | O | O | O | O | O | O | O | O | O | O | O |
| G | O | X* | O | X* | X | X* | O | X* | O | X* | X | X* |
| H | O | O | O | O | O | O | O | O | O | O | O | O |
| 1 | Failure - mold growth prior to starting Preservative Efficacy Testing | | | | | | | | | | | |
| J | Failure - mold growth prior to starting Preservative Efficacy Testing | | | | | | | | | | | |
| K | Failure - mold growth prior to starting Preservative Efficacy Testing | | | | | | | | | | | |
| L | Failure - mold growth prior to starting Preservative Efficacy Testing | | | | | | | | | | | |
| M | Failure - mold growth prior to starting Preservative Efficacy Testing | | | | | | | | | | | |
| N | Failure - mold growth prior to starting Preservative Efficacy Testing | | | | | | | | | | | |

Reviewing Table 5 demonstrates the synergistic results for antimicrobial activity of combining an acyl lactylate with a glycol. For example, Samples I-N only included either an acyl lactylate or a glycol mixed with a carrier of 99.5% water and pH adjusted to 4.5 with citric acid. As shown in Table 5, all of Samples I-N included microbial growth prior to even starting the Preservative Efficacy Test, such that the Preservative Efficacy Testing was not even conducted for those samples. All the other samples that included a combination of an acyl lactylate and a glycol (with one exception of Sample A), however, had at least some antimicrobial efficacy against various species of bacteria tested.

Surprisingly, two samples (Samples F and H) were able to achieve a passing result on the Preservative Efficacy Testing without the use of a traditional preservative being used in the composition. These samples included the combination of Sodium Caproyl/Lauroyl Lactylate and 1,2-Hexanediol (Sample F) and Sodium Lauroyl Lactylate and 1,2-Hexanediol (Sample H). While these two samples were the only two samples to pass the Preservative Efficacy Testing, Samples B, C, D, E, and G included various levels of antimicrobial activity. It is contemplated that Samples B, C, D, E, and G could be modified to include a traditional preservative to enhance the antimicrobial activity of the composition such that the compositions would pass the Preservative Efficacy Testing. In such a scenario, the acyl lactylate and glycol combination of Samples B, C, D, E, and G could provide the benefit of being able to reduce the amount of traditional preservative needed to achieve a satisfactory antimicrobial effect as compared to standard compositions that rely solely on a traditional preservative to achieve the antimicrobial effect. Reducing the amount of traditional preservative in a composition can help improve the water solubility of the composition, potentially increase the stability of such compositions, reduce potential for irritation, and provide an increase in social acceptability.

The actual results from the Preservative Efficacy Testing for Samples F and H are shown below in Tables 6 and 7, respectively.

TABLE 6

Preservative Efficacy Testing results for Sample F

| Organism | Initial | Day 7 | Day 14 | Day 28 |
|---|---|---|---|---|
| | | CFU/gram or mL | | |
| S. aureus | 6.0E+05 | <10 | <10 | <10 |
| E. coli | 3.4E+05 | <10 | <10 | <10 |
| P. aeruginosa | 1.9E+05 | <10 | <10 | <10 |
| C. albicans | 3.6E+05 | <10 | <10 | <10 |
| A. brasiliensis | 3.4E+05 | 17,000 | 12,500 | 12,500 |
| B. cepacia | 5.0E+05 | <10 | <10 | <10 |

TABLE 7

Preservative Efficacy Testing results for Sample H

| Organism | Initial | Day 7 | Day 14 | Day 28 |
|---|---|---|---|---|
| | | CFU/gram or mL | | |
| S. aureus | 6.0E+05 | <10 | <10 | <10 |
| E. coli | 3.4E+05 | <10 | <10 | <10 |
| P. aeruginosa | 1.9E+05 | <10 | <10 | <10 |
| C. albicans | 3.6E+05 | >25,000 | 260,000 | 26,000 |
| A. brasiliensis | 3.4E+05 | 195,000 | 165,000 | 230,000 |
| B. cepacia | 5.0E+05 | <10 | <10 | <10 |

As noted by comparing Tables 6 and 7, Sample F provided overall more antimicrobial activity against the fungicides of C. albicans and A. brasiliensis. However, it was observed that Sample F, which included Sodium Caproyl/Lauroyl Lactylate, had a strong chemical odor that may provide a negative experience in some product environments for a consumer and/or a user. Compositions including Sodium Caproyl/Lauroyl Lactylate (such as Sample F) could be modified to include a fragrance to offset or reduce the inherent odor.

The acyl lactylate of the antimicrobial compositions of the present disclosure can provide from about 0.01% to about 5.0% (by total weight of the composition), and more preferably from about 0.1% to about 1.0% (by total weight of the composition). The glycol of the antimicrobial composition of the present disclosure can provide from about 0.01% to about 5.0% (by total weight of the composition), and more preferably from about 0.1% to about 1.0% (by total weight of the composition). In some embodiments, a ratio of the acyl lactylate:glycol in the antimicrobial composition (as measured by weight) can be between about 0.5:1 to about 3:1, and more preferably from about 0.66:1 to about 2.3:1.

Carriers

As mentioned above, the antimicrobial compositions of the present disclosure that include an acyl lactylate and a glycol may be formulated with one or more conventional and compatible carrier materials. The antimicrobial composition may take a variety of forms including, without limitation, aqueous solutions, gels, balms, lotions, suspensions, creams, milks, salves, ointments, sprays, emulsions, oils, resins, foams, solid sticks, aerosols, and the like. Liquid carrier materials suitable for use in the instant disclosure include those well-known for use in the cosmetic, pharmaceutical, and medical arts as a basis for ointments, lotions, creams, salves, aerosols, gels, suspensions, sprays, foams, washes, and the like, and may be used in their established levels. The carrier can comprise from about 0.01% to about 99.98% (by total weight of the composition), depending on the carrier used.

Preferable carrier materials include polar solvent materials, such as water. For instance, where the antimicrobial composition is a wetting composition, such as described below for use with a wet wipe, the composition will typically include water. The antimicrobial compositions can suitably comprise water in an amount of from about 0.01% (by total weight of the composition) to about 99.98% (by total weight of the composition), or from about 1.00% (by total weight of the composition) to about 99.98% (by total weight of the composition), or from about 50.00% (by total weight of the composition) to about 99.98% (by total weight of the composition), or from about 75.00% (by total weight of the composition) to about 99.98% (by total weight of the composition). In some embodiments, water can comprise an amount from about 50.00% (by total weight of the composition) to about 70.00% (by total weight of the composition). In some embodiments, water can comprise an amount greater than 90.00% (by total weight of the composition). In some embodiments, water can comprise at least about 91%, or at least about 92%, or at least about 93%, or at least about 94%, or at least about 95%, or at least about 96%, or at least about 97%, or at least about 98%, or at least about 99% (by total weight of the composition).

Other potential carriers include emollients, humectants, polyols, surfactants, esters, perfluorocarbons, silicones, and other pharmaceutically acceptable carrier materials. In one embodiment, the carrier is volatile, allowing for immediate deposition of the antimicrobial ingredient to the desired surface while improving overall usage experience of the product by reducing drying time. Non-limiting examples of these volatile carriers include 5 cst Dimethicone, Cyclomethicone, Methyl Perfluoroisobutyl Ether, Methyl Perfluorobutyl Ether, Ethyl Perfluoroisobutyl Ether and Ethyl Perfluorobutyl Ether. Unlike conventional volatile carriers such as ethanol or isopropyl alcohol, these carriers have no antimicrobial effect.

In one embodiment, the antimicrobial compositions can optionally include one or more emollients, which typically act to soften, soothe, and otherwise lubricate and/or moisturize the skin. Suitable emollients that can be incorporated into the compositions include oils such as alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, fatty acids, glycerol esters and derivatives, propylene glycol esters and derivatives, alkoxylated carboxylic acids, alkoxylated alcohols, fatty alcohols, and combinations thereof.

Some embodiments of the antimicrobial compositions may include one or more emollients in an amount of from about 0.01% (by total weight of the composition) to about 20% (by total weight of the composition), or from about 0.05% (by total weight of the composition) to about 10% (by total weight of the composition), or from about 0.10% (by total weight of the composition) to about 5% (by total weight of the composition).

In some embodiments, the antimicrobial compositions include one or more esters. The esters may be selected from cetyl palmitate, stearyl palmitate, cetyl stearate, isopropyl laurate, isopropyl myristate, isopropyl palmitate, and combinations thereof. The fatty alcohols include octyldodecanol, lauryl, myristyl, cetyl, stearyl, behenyl alcohol, and combinations thereof. The fatty acids can include, but are not limited to, capric acid, undecylenic acid, lauric acid, Myristic acid, palmitic acid, stearic acid, oleic acid, linoleic acid, arachidic acid, and behenic acid. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients. Other suitable ester compounds for use in the antimicrobial compositions or the present disclosure are listed in the *International Cosmetic Ingredient Dictionary and Handbook*, 11th Edition, CTFA, (January, 2006) ISBN-10: 1882621360, ISBN-13: 978-1882621361, and in the 2007 *Cosmetic Bench Reference*, Allured Pub. Corporation (Jul. 15, 2007) ISBN-10: 1932633278, ISBN-13: 978-1932633276, both of which are incorporated by reference herein to the extent they are consistent herewith.

Humectants that are suitable as carriers in the antimicrobial compositions of the present disclosure include, for example, glycerin, glycerin derivatives, hyaluronic acid, hyaluronic acid derivatives, betaine, betaine derivatives, amino acids, amino acid derivatives, glycosaminoglycans, glycols, polyols, sugars, sugar alcohols, hydrogenated starch hydrolysates, hydroxy acids, hydroxy acid derivatives, salts of PCA and the like, and combinations thereof. Specific examples of suitable humectants include honey, sorbitol, hyaluronic acid, sodium hyaluronate, betaine, lactic acid, citric acid, sodium citrate, glycolic acid, sodium glycolate, sodium lactate, urea, propylene glycol, butylene glycol, pentylene glycol, ethoxydiglycol, methyl gluceth-10, methyl gluceth-20, polyethylene glycols (as listed in the *International Cosmetic Ingredient Dictionary and Handbook* such as PEG-2 through PEG 10), propanediol, xylitol, maltitol, or combinations thereof.

The antimicrobial compositions of the disclosure may include one or more humectants in an amount of about 0.01% (by total weight of the composition) to about 20% (by total weight of the composition), or about 0.05% (by total weight of the composition) to about 10% by total weight of the composition), or about 0.1% (by total weight of the composition) to about 5.0% (by total weight of the composition).

In an embodiment where the antimicrobial composition serves as a wash (e.g. shampoo; surface cleaner; or hand, face, or body wash), the antimicrobial composition will likely include one or more surfactants. In an embodiment where the antimicrobial composition is included in a wipe, the antimicrobial composition may also likely include one or more surfactants. These may be selected from anionic, cationic, nonionic, zwitterionic, and amphoteric surfactants. Amounts of surfactants may range from 0.01 to 30%, or from 0.05 to 20%, or from 0.10 to 15% by total weight of the composition. In some embodiments, the surfactant can comprise less than 1% by total weight of the composition.

Suitable anionic surfactants include, but are not limited to, $C_8$ to $C_{22}$ alkane sulfates, ether sulfates and sulfonates. Among the suitable sulfonates are primary $C_8$ to $C_{22}$ alkane sulfonate, primary $C_8$ to $C_{22}$ alkane disulfonate, $C_8$ to $C_{22}$ alkene sulfonate, $C_8$ to $C_{22}$ hydroxyalkane sulfonate or alkyl glyceryl ether sulfonate. Specific examples of anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate and mixtures thereof. Other anionic surfactants include the $C_8$ to $C_{22}$ acyl glycinate salts. Suitable glycinate salts include sodium cocoylglycinate, potassium cocoylglycinate, sodium lauroylglycinate, potassium lauroylglycinate, sodium myristoylglycinate, potassium myristoylglycinate, sodium palmitoylglycinate, potassium palmitoylglycinate, sodium stearoylglycinate, potassium stearoylglycinate, ammonium cocoylglycinate and mixtures thereof. Cationic counter-ions to form the salt of the glycinate may be selected from sodium, potassium, ammonium, alkanolammonium and mixtures of these cations.

Suitable cationic surfactants include, but are not limited to alkyl dimethylamines, alkyl amidopropylamines, alkyl imidazoline derivatives, quaternised amine ethoxylates, and quaternary ammonium compounds.

Suitable nonionic surfactants include, but are not limited to, alcohols, acids, amides or alkyl phenols reacted with alkylene oxides, especially ethylene oxide either alone or with propylene oxide. Specific nonionics are $C_6$ to $C_{22}$ alkyl phenols-ethylene oxide condensates, the condensation products of $C_8$ to $C_{13}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides, alkyl polysaccharides, amine oxides, block copolymers, castor oil ethoxylates, ceto-oleyl alcohol ethoxylates, ceto-stearyl alcohol ethoxylates, decyl alcohol ethoxylates, dinonyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, mono-branched alcohol ethoxylates, natural alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, synthetic alcohol ethoxylates, tall oil fatty acid ethoxylates, tallow amine ethoxylates and trid tridecanol ethoxylates.

Suitable zwitterionic surfactants include, for example, alkyl amine oxides, alkyl hydroxysultaines, silicone amine oxides, and combinations thereof. Specific examples of suitable zwitterionic surfactants include, for example, 4-[N,N-di(2-hydroxyethyl)-N-octadecylammonio]-butane-1-carboxylate, S—[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, lauryl hydroxysultaine and combinations thereof.

Suitable amphoteric surfactants include, but are not limited to, derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative amnphoterics are coco dimethyl carboxymethyl betaine, cocoamidopropyl betaine, coco-betaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, cocoamphoacetates, and combinations thereof. The sulfobetaines may include stearyl dimethyl sulfopropyl betaine, lauryl dimethyl sulfoethyl betaine, lauryl bis-(2-hydroxyethyl) sulfopropyl betaine and combinations thereof.

Rheology Modifier

Optionally, one or more rheology modifiers, such as thickeners, may be added to the antimicrobial compositions. Suitable rheology modifiers are compatible with the antimicrobial agent. As used herein, "compatible" refers to a compound that, when mixed with the antimicrobial agent, does not adversely affect the antimicrobial properties of same.

A thickening system is used in the antimicrobial compositions to adjust the viscosity and stability of the compositions. Specifically, thickening systems prevent the composition from running off of the hands or body during dispensing and use of the composition. When the antimicrobial composition is used with a wipe product, a thicker formulation can be used to prevent the composition from migrating from the wipe substrate.

The thickening system should be compatible with the compounds used in the present disclosure; that is, the thickening system, when used in combination with the antimicrobial compounds, should not precipitate out, form a coacervate, or prevent a user from perceiving the conditioning benefit (or other desired benefit) to be gained from the composition. The thickening system may include a thickener which can provide both the thickening effect desired from the thickening system and a conditioning effect to the user's skin.

Thickeners may include, cellulosics, gums, acrylates, starches and various polymers. Suitable examples include but are not limited to hydroxethyl cellulose, xanthan gum, guar gum, potato starch, and corn starch. In some embodiments, PEG-150 stearate, PEG-150 distearate, PEG-175 diisostearate, polyglyceryl-10 behenate/eicosadioate, disteareth-100 IPDI, polyacrylamidomethylpropane sulfonic acid, butylated PVP, and combinations thereof may be suitable.

While the viscosity of the compositions will typically depend on the thickener used and the other components of the compositions, the thickeners of the compositions suitably provide for a composition having a viscosity in the range of greater than 1 cP to about 30,000 cP or more. In another embodiment, the thickeners provide compositions having a viscosity of from about 100 cP to about 20,000 cP. In yet another embodiment, thickeners provide compositions having a viscosity of from about 200 cP to about 15,000 cP. In embodiments where the compositions are included in a wipe, the viscosity may range from about 1 cP to about 2000 cP.

Typically, the antimicrobial compositions of the present disclosure include the thickening system in an amount of no more than about 20% (by total weight of the composition), or from about 0.01% (by total weight of the composition) to about 20% (by total weight of the composition). In another aspect the thickening system is present in the antimicrobial composition in an amount of from about 0.10% (by total weight of the composition) to about 10% (by total weight of the composition), or from about 0.25% (by total weight of the composition) to about 5% (by total weight of the composition), or from about 0.5% (by total weight of the composition) to about 2% (by total weight of the composition).

Emulsifiers

In one embodiment, the antimicrobial compositions may include hydrophobic and hydrophilic ingredients, such as a lotion or cream. Generally, these emulsions have a dispersed phase and a continuous phase, and are generally formed with the addition of a surfactant or a combination of surfactants with varying hydrophilic/lipopiliclipophilic balances (HLB). Suitable emulsifiers include surfactants having HLB values from 0 to 20, or from 2 to 18. Suitable non-limiting examples include Ceteareth-20, Cetearyl Glucoside, Ceteth-10, Ceteth-2, Ceteth-20, Cocamide MEA, Glyceryl Laurate, Glyceryl Stearate, PEG-100 Stearate, Glyceryl Stearate, Glyceryl Stearate SE, Glycol Distearate, Glycol Stearate, lsosteareth-20, Laureth-23, Laureth-4, Lecithin, Methyl Glucose Sesquistearate, Oleth-10, Oleth-2, Oleth-20, PEG-100 Stearate, PEG-20 Almond Glycerides, PEG-20 Methyl Glucose Sesquistearate, PEG-25 Hydrogenated Castor Oil, PEG-30 Dipolyhydroxystearate, PEG-4 Dilaurate, PEG-40 Sorbitan Peroleate, PEG-60 Almond Glycerides, PEG-7 Olivate, PEG-7 Glyceryl Cocoate, PEG-8 Dioleate, PEG-8 Laurate, PEG-8 Oleate, PEG-80 Sorbitan Laurate, Polysorbate 20, Polysorbate 60, Polysorbate 80, Polysorbate 85, Propylene Glycol Isostearate, Sorbitan Isostearate, Sorbitan Laurate, Sorbitan Monostearate, Sorbitan Oleate, Sorbitan Sesquioleate, Sorbitan Stearate, Sorbitan Trioleate, Stearamide MEA, Steareth-100, Steareth-2, Steareth-20, Steareth-21. The compositions can further include surfactants or combinations of surfactants that create liquid crystalline networks or liposomal networks. Suitable non-limiting examples include OLIVEM 1000 (INCI: Cetearyl Olivate (and) Sorbitan Olivate (available from HallStar Company (Chicago, Ill.)); ARLACEL LC (INCI: Sorbitan Stearate (and) Sorbityl Laurate, commercially available from Croda (Edison, N.J.)); CRYSTALCAST MM (INCI: Beta Sitosterol (and) Sucrose Stearate (and) Sucrose Distearate (and) Cetyl Alcohol (and) Stearyl Alcohol, commercially available from MMP Inc. (South Plainfield, N.J.)); UNIOX CRISTAL (INCI: Cetearyl Alcohol (and) Polysorbate 60 (and) Cetearyl Glucoside, commercially available from Chemyunion (Sao Paulo, Brazil)). Other suitable emulsifiers include lecithin, hydrogenated lecithin, lysolecithin, phosphatidylcholine, phospholipids, and combinations thereof.

Adjunct Ingredients

The antimicrobial compositions of the present disclosure may additionally include adjunct ingredients conventionally found in cosmetic, pharmaceutical, medical, or personal care compositions/products in an established fashion and at established levels. For example, the antimicrobial compositions may comprise additional compatible pharmaceutically active and compatible materials for combination therapy, such as antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, and combinations thereof.

Other suitable additives that may be included in the antimicrobial compositions of the present disclosure include compatible colorants, deodorants, emulsifiers, anti-foaming agents (when foam is not desired), lubricants, skin conditioning agents, skin protectants and skin benefit agents (e.g., aloe vera and tocopheryl acetate), solvents, solubilizing agents, suspending agents, wetting agents, pH adjusting ingredients (a suitable pH range of the compositions can be from about 3.5 to about 8), chelators, propellants, dyes and/or pigments, and combinations thereof.

Another component that may be suitable for addition to the antimicrobial compositions is a fragrance. Any compatible fragrance may be used. Typically, the fragrance is present in an amount from about 0% (by weight of the composition) to about 5% (by weight of the composition), and more typically from about 0.01% (by weight of the composition) to about 3% (by weight of the composition). In one desirable embodiment, the fragrance will have a clean, fresh and/or neutral scent to create an appealing delivery vehicle for the end consumer.

Organic sunscreens that may be present in the antimicrobial compositions include ethylhexyl methoxycinnamate, avobenzone, octocrylene, benzophenone-4, phenylbenzimidazole sulfonic acid, homosalate, oxybenzone, benzophenone-3, ethylhexyl salicylate, and mixtures thereof.

In addition to the combination of the acyl lactylates and glycols as discussed herein, the antimicrobial composition may also include various combinatorial preservatives to increase shelf life. Some suitable combinatorial preservatives that may be used in the present disclosure include traditional preservatives. As used herein, "traditional preservatives" means compounds that have been historically recognized by regulatory bodies as providing preservative or antimicrobial effect, such as those listed in the European Union's Annex V list of preservatives allowed in cosmetics products. Traditional preservatives include, but are not limited to: propionic acid and salts thereof; salicylic acid and salts thereof; sorbic acid and salts thereof; benzoic acid and salts and esters thereof; formaldehyde; paraformaldehyde; o-phenylphenol and salts thereof; zinc pyrithione; inorganic sulfites; hydrogen sulfites; chlorobutanol; benzoic parabens, such as methylparaben, propylparaben, butylparaben, ethylparaben, isopropylparaben, isobutylparaben, benzylparaben, sodium methylparaben and sodium propylparaben; dehydroacetic acid and salts thereof; formic acid and salts thereof; dibromohexamidine isethionate; thimerosal; phenylmercuric salts; undecylenic acid and salts thereof; hexetidine; 5-bromo-5-nitro-1,3-dioxane; 2-bromo-2-nitropropane-1,3,-diol; dichlorobenzyl alcohol; triclocarban; p-chloro-m-cresol; triclosan; chloroxylenol; imidazolidinyl urea; polyaminopropyl biguanide; phenoxyethanol, methenamine; quaternium-15; climbazole; DMDM hydantoin; benzyl alcohol; piroctone olamine; bromochlorophene; o-cymen-5-ol; methylchloroisothiazolinone; methylisothiazolinone; chlorophene; chloroacetamide; chlorhexidine; chlorhexidine diacetate; chlorhexidine digluconate; chlorhexidine dihydrochloride; phenoxyisopropanol; alkyl (C12-C22) trimethyl ammonium bromide and chlorides; dimethyl oxazolidine; diazolidinyl urea; hexamidine; hexamidine diisethionate; glutaral; 7-ethylbicyclooxazolidine; chlorphenesin; sodium hydroxymethylglycinate; silver chloride; benzethonium chloride; benzalkonium chloride; benzalkonium bromide; benzylhemiformal; iodopropynyl butylcarbamate; ethyl lauroyl arginate HCl; citric acid and silver citrate.

Other combinatorial preservatives that may be added to the antimicrobial compositions of the present disclosure include non-traditional preservatives that are known to exhibit antimicrobial effects in addition to their primary functions, but that have not historically been recognized as preservatives by regulatory bodies (such as on the European Union's Annex V list). Examples of these non-traditional antimicrobial ingredients include, but are not limited to, hydroxyacetophenone, caprylyl glycol, sodium coco-PG dimonium chloride phosphate, phenylpropanol, lactic acid and salts thereof, caprylhydroxamic acid, levulinic acid and salts thereof, sodium lauroyl lactylate, phenethyl alcohol, sorbitan caprylate, glyceryl caprate, glyceryl caprylate, ethylhexylglycerin, p-anisic acid and salts thereof, gluconolactone, decylene glycol, 1,2-hexanediol, glucose oxidase and lactoperoxidase, leuconostoc/radish root ferment filtrate and glyceryl laurate.

The amount of the combinatorial preservatives in the antimicrobial compositions is dependent on the relative amounts of other components present within the composition. For example, in some embodiments, the combinatorial preservative is present in the compositions in an amount between about 0.001% to about 5% (by total weight of the composition), in some embodiments between about 0.01 to about 3% (by total weight of the composition), and in some embodiments, between about 0.05% to about 1.0% (by total weight of the composition). In some embodiments, the combinatorial preservative can be present in the composition in an amount less than 0.2% (by total weight of the composition).

However, in some embodiments, the antimicrobial composition is substantially free of any combinatorial preservative (either a traditional preservative or a non-traditional preservative), yet still provides adequate efficacy against microbial growth. As used herein, "substantially free" of any combinatorial preservative means the composition includes less than 10 ppm, or 0.001% (by total weight of the composition), of a combinatorial preservative. Thus, in some embodiments, the antimicrobial composition does not include a traditional preservative or a non-traditional preservative. As discussed above, Samples F and H provided two embodiments that had successful antimicrobial efficacy without the utilization of any traditional preservatives.

Delivery Vehicles

The antimicrobial compositions of the present disclosure may be used in combination with a product that can serve as a delivery vehicle for the antimicrobial composition. For example, the antimicrobial composition may be incorporated into or onto a substrate, such as a wipe substrate, an absorbent substrate, a fabric or cloth substrate, a tissue or paper towel substrate, or the like. In one embodiment, the antimicrobial composition may be used in combination with a wipe substrate to form a wet wipe or may be a wetting composition for use in combination with a wipe which may be dispersible. In other embodiments, the antimicrobial composition may be incorporated into wipes such as wet wipes, hand wipes, face wipes, cosmetic wipes, cloths and the like. In yet other embodiments, the antimicrobial compositions described herein can be used in combination with numerous personal care products, such as absorbent articles. Absorbent articles of interest are diapers, training pants, adult incontinence products, feminine hygiene products, and the like; bath or facial tissue; and paper towels. Personal protective equipment articles of interest include but are not limited to masks, gowns, gloves, caps, and the like.

In one embodiment, the wet wipe may comprise a nonwoven material that is wetted with an aqueous solution termed the "wetting composition," which may include or be composed entirely of the antimicrobial compositions disclosed herein. As used herein, the nonwoven material comprises a fibrous material or substrate, where the fibrous material or substrate comprises a sheet that has a structure of individual fibers or filaments randomly arranged in a mat-like fashion. Nonwoven materials may be made from a variety of processes including, but not limited to, airlaid processes, wet-laid processes such as with cellulosic-based tissues or towels, hydroentangling processes, staple fiber carding and bonding, melt blown, and solution spinning.

When the antimicrobial composition is added to a delivery vehicle, such as a wipe substrate, the amount of add-on of the antimicrobial composition can range from about 100% to about 400%, or more preferably from about 200% to about 375%, or even more preferably from about 240% to about 350%. In some embodiments, the add-on of the antimicrobial composition can be from 200% to about 350%. In one particular embodiment, the add-on can be about 330%.

The fibers forming the fibrous material may be made from a variety of materials including natural fibers, synthetic fibers, and combinations thereof. The choice of fibers may depend upon, for example, the intended end use of the finished substrate and the fiber cost. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or crosslinked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber.

Airlaid nonwoven fabrics are particularly well suited for use as wet wipes. The basis weights for airlaid nonwoven fabrics may range from about 20 to about 200 grams per square meter (gsm) with staple fibers having a denier of about 0.5 to about 10 and a length of about 6 to about 15 millimeters. Wet wipes may generally have a fiber density of about 0.025 g/cc to about 0.2 g/cc. Wet wipes may generally have a basis weight of about 20 gsm to about 150 gsm. More desirably the basis weight may be from about 30 to about 90 gsm. Even more desirably the basis weight may be from about 50 gsm to about 75 gsm.

Processes for producing airlaid non-woven basesheets are described in, for example, published U.S. Pat. App. No. 2006/0008621, herein incorporated by reference to the extent it is consistent herewith.

Test Methods

Preservative Efficacy Testing

The Preservative Efficacy Testing discussed herein was completed pursuant to the standard antimicrobial effectiveness test from Chapter 51 of the United States Pharmacopeia (USP 51), in which an antimicrobial composition can be tested against at least five microorganisms, including bacteria and fungi. In the Preservative Efficacy Testing conducted herein, the following bacteria were utilized: *Staphylococcus aureus, Escherichia coli, Pseudomonas aeruginosa,* and *Burkholderia cepacia*; and the following fungi were utilized: *Candida albicans,* and *Aspergillus brasiliensis*. While one of ordinary skill in the art could replicate such Preservative Efficacy Testing by completing USP 51 protocol, a brief summary was that each antimicrobial composition sample was tested against each microorganism being held at room temperature over the course of 28 days, with each sample being evaluated at specific intervals at the beginning of the Testing (initial), day 7, day 14, and day 28. The test sample colonies were counted at each interval to determine the number of surviving microorganisms. The log reduction of each microorganism at each interval was reported. The effectiveness of the antimicrobial agent sample was based on the USP 51 passing criteria.

EMBODIMENTS

Embodiment 1: A composition comprising: an acyl lactylate; a glycol; and a carrier, wherein the carrier comprises water; wherein water comprises at least about 90% by weight of the composition.

Embodiment 2: The composition of embodiment 1, wherein the acyl lactylate is selected from the group consisting of: Sodium Isostearyl Lactylate, Sodium Caproyl/Lauroyl Lactylate, and Sodium Lauroyl Lactylate, and combinations thereof.

Embodiment 3: The composition of embodiment 1 or 2, wherein the glycol is selected from the group consisting of: Propylene Glycol, 1,2-Hexanediol, Methylpropanediol, Isopentyldiol, and combinations thereof.

Embodiment 4: The composition of embodiment 3, wherein the acyl lactylate is Sodium Caproyl/Lauroyl Lactylate.

Embodiment 5: The composition of embodiment 1, wherein the acyl lactylate is Sodium Isostearyl Lactylate and the glycol is Propylene Glycol or 1,2-Hexanediol.

Embodiment 6: The composition of embodiment 1, wherein the acyl lactylate is Sodium Lauroyl Lactylate and the glycol is Propylene Glycol or 1,2-Hexanediol.

Embodiment 7: The composition of any one of the preceding embodiments, wherein a ratio of acyl lactylate:glycol is between about 0.66:1 and 2.3:1.

Embodiment 8: The composition of any one of the preceding embodiments, wherein the acyl lactylate comprises from about 0.1 to about 1.0% by weight of the composition, wherein the glycol comprises from about 0.1 to about 1.0% by weight of the composition, and wherein the water comprises no more than about 99.8% by weight of the composition.

Embodiment 9: The composition of any one of the preceding embodiments, further comprising a pH adjusting ingredient, and wherein a pH of the composition is less than 5.

Embodiment 10: The composition of any one of the preceding embodiments, wherein the composition is substantially free from a traditional preservative.

Embodiment 11: A composition consisting of: an acyl lactylate; a glycol; a carrier, wherein the carrier comprises water; wherein water forms between about 90% and about 99.8% by weight of the composition; and one or more optional ingredients selected from the group consisting of a pH adjusting ingredient and a fragrance.

Embodiment 12: The composition of embodiment 11, wherein the acyl lactylate is selected from the group consisting of: Sodium Isostearyl Lactylate, Sodium Caproyl/Lauroyl Lactylate, and Sodium Lauroyl Lactylate, and combinations thereof, and wherein the glycol is selected from the group consisting of: Propylene Glycol, 1,2-Hexanediol, Methylpropanediol, Isopentyldiol, and combinations thereof.

Embodiment 13: A wipe comprising: a substrate; and a composition applied to the substrate, the composition comprising: an acyl lactylate; a glycol; and a carrier, wherein the carrier comprises water; wherein water comprises at least about 50% by weight of the composition.

Embodiment 14: The wipe of embodiment 13, wherein the acyl lactylate is selected from the group consisting of: Sodium Isostearyl Lactylate, Sodium Caproyl/Lauroyl Lactylate, and Sodium Lauroyl Lactylate, and combinations thereof; and wherein the glycol is selected from the group consisting of: Propylene Glycol, 1,2-Hexanediol, Methylpropanediol, Isopentyldiol, and combinations thereof.

Embodiment 15: The wipe of embodiment 13, wherein acyl lactylate is Sodium Caproyl/Lauroyl Lactylate or Sodium Lauroyl Lactylate, and wherein the glycol is 1,2-Hexanediol.

Embodiment 16: The wipe of any one of embodiments 13-15, wherein the composition is applied to the substrate at an add-on percentage of about 200% to about 350%.

Embodiment 17: A method of inhibiting microbial growth in a product, the method comprising: providing a composition, the composition comprising: an acyl lactylate; a glycol; and a carrier; providing a product; and applying the composition to the product to inhibit microbial growth in the product.

Embodiment 18: The method of embodiment 17, wherein the product is selected from the group consisting of: shampoo, conditioner, soaps, moisturizers, skin protective, skin restorative and skin strengthening products, hand sanitizers, skin and body cleansers, deodorants, sunscreens, lip balms, lip sticks, wipes, facial tissue, bath tissue, paper towels, napkins, diapers, diaper pants, feminine hygiene products gloves, socks, masks or a combination thereof.

Embodiment 19: The method of embodiment 17 or 18, wherein the acyl lactylate is selected from the group consisting of: Sodium Isostearyl Lactylate, Sodium Caproyl/Lauroyl Lactylate, and Sodium Lauroyl Lactylate, and combinations thereof.

Embodiment 20: The method of any one of embodiments 17-19, wherein the glycol is selected from the group consisting of: Propylene Glycol, 1,2-Hexanediol, Methylpropanediol, Isopentyldiol, and combinations thereof.

Embodiment 21: The method of embodiment 20, wherein the acyl lactylate is Sodium Caproyl/Lauroyl Lactylate.

Embodiment 22: The method of embodiment 17 or 18, wherein the acyl lactylate is Sodium Isostearyl Lactylate and the glycol is Propylene Glycol or 1,2-Hexanediol.

Embodiment 23: The method of embodiment 17 or 18, wherein the acyl lactylate is Sodium Lauroyl Lactylate and the glycol is Propylene Glycol or 1,2-Hexanediol.

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the disclosure.

What is claimed is:

1. A composition consisting of:
   an acyl lactylate;
   a glycol;
   water; wherein water forms between about 90% and about 99.8% by weight of the composition; and
   optionally one or more ingredients selected from the group consisting of a pH adjusting ingredient and a fragrance.

2. The composition of claim 1, wherein the acyl lactylate is selected from the group consisting of: Sodium Isostearyl Lactylate, Sodium Caproyl/Lauroyl Lactylate, and Sodium Lauroyl Lactylate, and combinations thereof, and wherein the glycol is selected from the group consisting of: Propylene Glycol, 1,2-Hexanediol, Methylpropanediol, Isopentyldiol, and combinations thereof.

* * * * *